United States Patent [19]

Larock

[11] 4,010,170
[45] Mar. 1, 1977

[54] BUTENOLIDE SYNTHESIS VIA CARBONYLATION OF VINYLMERCURIALS

[75] Inventor: Richard Craig Larock, Ames, Iowa

[73] Assignee: Iowa State University Research Foundation, Inc., Ames, Iowa

[22] Filed: Sept. 24, 1975

[21] Appl. No.: 616,436

[52] U.S. Cl. .......................................... 260/343.6
[51] Int. Cl.² ...................................... C07D 307/58
[58] Field of Search ............................... 260/343.6

[56] References Cited
OTHER PUBLICATIONS

Murakami et al., Mem. Inst. Sci. Ind. Research Osaka Univ. 16, 219–230 (1959), (cited as C.A. 54:22555–22556).
Hata et al., Nippon Kagaku Zasshi, 79, 1531–1537 (1958), (cited as C.A. 54:24619–24620).
Mabry, J. Org. Chem. 28, 1699–1700 (1963), (cited as C.A. 59:3854(1963)).

*Primary Examiner*—Henry R. Jiles
*Assistant Examiner*—C. M. S. Jaisle
*Attorney, Agent, or Firm*—Zarley, McKee, Thomte & Voorhees

[57] ABSTRACT

Compounds containing the butenolide ring have a wide variety of chemical uses. The invention is a method of synthesizing β-halobutenolides which are valuable intermediates in preparing a variety of butenolide ring containing compounds. The method comprises reacting an acetylenic alcohol with a mercuric halide to provide a vinylmercuric halide and carbonylating the vinylmercuric halide to provide a β-halobutenolide.

11 Claims, No Drawings

1 …

BUTENOLIDE SYNTHESIS VIA CARBONYLATION OF VINYLMERCURIALS

BACKGROUND OF THE INVENTION

Compounds containing the butenolide ring which has the basic formula:

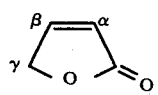

occur widely in nature and often possess an unusual range of biological activities. They appear throughout the plant kingdom from the simple metabolites of lichens, mold and fungi, to the more complex sesquiterpenes of the family Compositae and steriodal glycosides of the families Ranunculaceae, Liliaceae, Scrophulariaceae, and Apocyanaceae. More recently butenolides have been observed in such diverse animal species as sponges, and insects. In the latter species they may play a significant role as chemical defense weapons.

Certain butenolide ring containing compounds are useful as insecticides, herbicides, and seed and plant growth regulators. Of considerable importance also is the widespread characteristic among butenolide containing compounds of allergenic, antibacterial, and antifungal activity.

Undoubtedly, Vitamin C is the most physiologically important butenolide ring containing compound. Other uses for certain butenolide ring containing compounds include recently reported uses of cardiac glycosides as having the unusual characteristics of reducing the frequency of the heartbeat but increasing the amplitude of the heartbeat.

The unusual range of usefulness of compounds containing the basic butenolide ring has stimulated considerable research on the synthesis of these valuable compounds. While numerous methods have been reported in the literature for the preparation for butenolides, see for example, Y. S. Rao, Chem. Rev., 64, 353 (1964); W. E. Epstein and A. C. Sonntag, J. Org. Chem., 32, 3390 (1967); K. Iwai, M. Kawai, H. Kosugi and H. Uda, Chem. Lett., 385 (1974); and K. Iwai, H. Kosugi and H. Uda, Chem. Lett., 1237 (1974), these methods all generally suffer from several disadvantages. Some of these disadvantages include inaccessibility of the starting materials, the necessity for employing severe reaction conditions, the very low yields of product obtained, and generally limited versatility in preparing the desired butenolide ring containing compounds.

Accordingly, one object of this invention is to provide a general synthesis route which has universal application for preparing a wide variety of butenolide ring containing compounds.

Another object of this invention is to provide a synthesis method for butenolide ring containing compounds which involves only a two-step synthesis and avoids the utilization of hydrogenation, Grignard reagents and other techniques often utilized by prior art synthesis methods.

Another object of this invention is to provide the compound β-chlorobutenolide and gamma substituted derivatives thereof.

Yet another object of this invention is to provide β-halobutenolides and gamma derivatives thereof, in unusually high yields, generally in excess of 90%.

Still another object is to replace the β halogen of β-halobutenolides to obtain β alkyl, aryl and vinyl butenolides.

SUMMARY OF THE INVENTION

This invention relates to a new convenient method of synthesis of butenolide ring containing compounds. More specifically, the invention relates to a new convenient synthesis method for preparation of β-halobutenolides, and more specifically, β-chlorobutenolide, a compound which is a valuable synthesis intermediate for synthesizing a wide variety of useful butenolide ring containing compounds. Moreover, the process of this invention provides β-chlorobutenolide or derivatives thereof in unusually high yields and in a simple two-step reaction procedure in contra-distinction to the prior art methods of preparing butenolides which involve a plurality of complicated steps, severe reaction conditions, and provided economically unsatisfactory low yields.

DETAILED DESCRIPTION OF THE INVENTION

In the first step of the process of this invention an acetylenic or more specifically a propargylic alcohol of the formula:

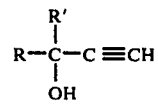

is reacted with a mercuric halide, of the formula: $HgX_2$ wherein X is selected from the group consisting of halides and is preferably chloride.

As can be seen from the above general formula for the acetylenic alcohol, when R and R' are hydrogen, the acetylenic alcohol is propargyl alcohol. From time to time the term "substituted acetylenic alcohol" will be utilized herein and it is understood that what is meant is propargyl alcohol wherein the hydrogen moieties for R and R' are substituted with alkyl or other appropriate groups as hereinafter explained.

The first step reaction may be represented by the following equation;

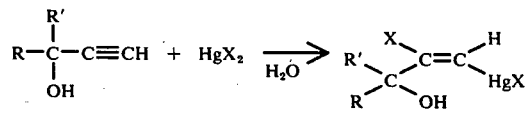

As can be seen from the immediately preceding equation, the acetylenic alcohol is reacted with mercuric chloride to provide a vinylmercuric chloride, and wherein R and R' are hydrogen with the starting acetylenic alcohol being propargyl alcohol, the product of the first step reaction is a trans-vinylmercuric chloride.

As can be appreciated, since the reaction of the acetylenic alcohol and the mercuric chloride is an equimolar addition reaction, it is preferred that at least equimolar amounts of each reactant be employed. It is also preferred that this reaction be conducted in an aqueous medium.

It is preferred that the mercuric halide be mercuric chloride because of its ease of solubility. Most preferably this first step reaction, set forth above, is conducted utilizing mercuric chloride in an aqueous medium which is comprised of a saturated solution of mercuric chloride in a sodium chloride solution in order to enhance the solubility characteristics of mercuric chloride. It is also preferred that the reaction be conducted in the presence of an excess of mercuric chloride in order to insure that the reaction is carried to completion.

No criticality exists with regard to the temperature employed during this first step reaction; however, for convenience purposes, it is preferred that the reaction be conducted at room temperature. In addition, there is no criticality with regard to the pressures employed during this first step reaction and preferably the pressure is simply atmospheric pressure. Likewise, there is no criticality with regard to the time of reacting for this first step reaction since the reaction is a substantially instantaneous addition reaction.

In a second step reaction, the vinylmercuric halide, or in the case where R and R' of the acetylenic alcohol are something other than hydrogen, a substituted vinylmercuric halide is carbonylated according to the following equation:

hol, ether, acetone and the like. It should, however, be understood that while the utilization or an organic polar solvent in the carbonylation-lactonization second-step reaction is preferred, if desired, the reaction can be carried out in the presence of aqueous solvent medium.

It is preferred that the carbonylation reaction be conducted by adding the noble metal halide, the lithium chloride, and the polar organic solvent together in a reaction flask. Thereafter, the reaction mixture may be cooled to low temperatures, as low as −78° C., and purged with a carbon monoxide atmosphere. While purging with carbon monoxide is occurring the vinylmercuric halide is added. After the entire amount of the vinylmercuric halide is added to the reaction mixture the reaction is thereafter allowed to gradually rise to room temperature. While low temperatures in the neighborhood of −20° C. to −78° C. are preferred, it should be understood that they are not critical and that the reaction can equally as well be carried out under ambient conditions.

As can be seen from an examination of both of the reaction steps set forth above, i.e., the first step reac-

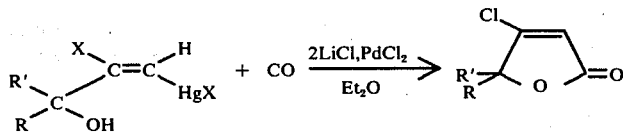

As can be seen, the carbonylation reaction involves a removal of the mercuric chloride moiety, HgX, from the vinyl-mercuric halide and the addition of the carbonyl group at the same situs followed by an internal esterification reaction closing the ring and forming the butenolide ring containing compound. The carbonylation reaction is preferably conducted in the presence of either a reaction equivalent amount of a noble metal salt and lithium chloride or alternatively and most preferably is a palladium catalyst promoted carbonylation reaction conducted in the presence of a reoxidant such as cupric chloride. However, it is to be understood that other noble metals can be utilized with equally satisfactory results, for example, platinum, iridium, rhodium, ruthenium and the like. Where the noble metal salt promotion is utilized, lithium chloride is thereafter involved in an exchange reaction with the palladium salt. Where the noble metal catalyst is employed the noble metal catalyst is either the noble metal on charcoal or a halide salt of a noble metal, for example, palladium chloride. Typically, in the catalytic promotion about 1% by weight of the catalyst is employed and two equivalents of the cupric chloride reoxidant are employed to reoxidize Pd° to Pd$^{2+}$. In summary, the carbonylation reaction is promoted by noble metals. Noble metal salts in combination with lithium chloride may be employed at reaction equivalent levels or alternatively catalytic amounts of the noble metal or its halide salts may be employed in the presence of a reoxidant such as cupric chloride.

The above discussed carbonylation reaction is preferably conducted in the presence of a polar organic solvent that is inert to the reactants employed in the carbonylation reaction, i.e., carbon monoxide and the vinylmercuric halide. The precise polar organic solvent employed is not critical and any of the conventional ones may be utilized such as ethyl alcohol, methyl alcotion of an acetylenic alcohol with a mercuric halide, followed by the second step of carbonylating the resulting vinylmercuric halide in the presence of a noble metal catalyst to provide a butenolide ring containing compound, the R and R' substituents on the acetylenic alcohol ultimately become gamma position moieties on the butenolide ring, after the carbonylation reaction occurs. Thus the precise value of R and R' for the acetylenic alcohol will depend upon what organic moieties are selected for the gamma position substituents on the butenolide compound. For example, where R and R' are hydrogen, the starting acetylenic alcohol is propargyl alcohol and the resulting butenolide compound is β-chloro-butenolide. Thus there is no precise criticality with regard to the substituents R and R' and they are in fact selected to build the desired butenolide ring containing compound for ultimate usage. Preferably, however, R and R' are selected from the group consisting of hydrogen, alkyls, aryls, substituted alkyls, substituted aryls, aralkyls and substituted aralkyls. For example, R and R' can be the following:

| R | R' |
|---|---|
| H | H |
| H | $CH_3$ |
| H | $C_4H_9$ |
| H | $C_6H_5$ |
| $CH_3$ | $CH_3$ |
| $C_6H_5$ | $C_6H_5$ |

As previously mentioned, the butenolide ring containing compounds have a variety of uses and the precise compound ultimately prepared will determine the values for the R and R' moieties of the acetylenic alcohol utilized in the first reaction discussed above. For example, the following table lists several known useful butenolide ring containing compounds which can be prepared by appropriate selection of R and R'.

| Butenolide Ring Containing Compound | Use | Value of R & R' Substitutents on the Acetylenic Alcohol |
|---|---|---|
| 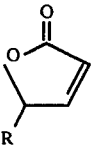 | Seed and plant growth regulators; also tobacco flavor and aroma ingredient. | R=CH₃ or C₂H₅ R'=H |
| 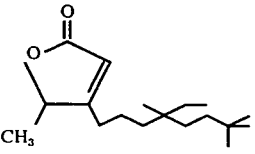 | Insecticide | R=CH₃ also substituted R'=H at 2 position |
| 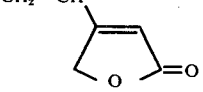 | Useful annelation reagent for the synthesis of tumor inhibiting sesquiterpene lactones | R=H; R'=H β=CH₂=CH (β substituted) |
| 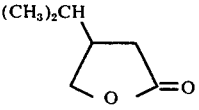 | Tobacco flavor and aroma ingredient | R and R'=H; substituted at 2 position with isopropyl |
| 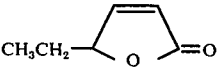 | Appears in raspberry oil; useful flavor and aroma ingredient | R'=H R=C₂H₅; also see first listing in table |

As seen from the previously described carbonylation equation, the resulting butenolide ring containing compound has a beta chlorine moiety. Since most butenolide ring containing compounds which are known to possess valuable properties do not contain a beta chlorine moiety, in many instances it is necessary to remove the beta position chlorine moiety. This can be done with a wide variety of reducing agents. For example, [H₂-Pd/C-HOAc-NaOAc, Li-t-C₄H₉OH-THF, Na(Hg)-,Na-NH₃, Na-t-C₄H₉OH-THF, Na-naphthalene, Mg-i-C₃H₇OH, Zn-HOAc, Zn(Ag)-CH₃OH, CrSO₄-DMF, Cr(ClO₄)₂-EDA, NaBH₄-hν, NaBH₄-PdCl₂, LiHAl-(OCH₃)₃-CuI, and Li(n-C₄H₉CuH). The most preferred reducing agent is: Zn(Ag)-CH₃OH. Of course, if desired, the beta chlorine position can be reduced to provide a hydrogen in this position or alternatively it provides an ideal site for an additional alkyl substitution. Thus, for example, a number of extremely important compounds most notably aglycones of the cardiac glycosides (cardenolides) possess alkyl substitutents in the beta position. Treatment of the beta chloro-butenolide with organocopper reagents will provide a broad array of such beta-substituted compounds. Such copper promoted alkylation reactions are already well known in other organic syntheses and will therefore not be described in detail herein. However, for further reference with regard to copper promoted alkylation reactions, see Posner, "Organic Reactions," J. Wiley, New York, which to the extent that it deals with copper alkylation reactions is incorporated specifically herein by reference.

The following examples are offered to further illustrate but not limit the invention disclosed herein.

EXAMPLE

Propargyl alcohol having the empirical formula HO-CH₂C≡CH was reacted with mercuric chloride in an aqueous solvent medium. The first step reaction was conducted in the following manner. A 50 milliliter saturated solution of sodium chloride and mercuric chloride was prepared at ambient temperatures. Sodium chloride was utilized in combination with mercuric chloride in order to increase the solubility of the mercuric chloride. The solution was thereafter cooled while 10 grams of propargyl alcohol was dripped in with rapid stirring. The reaction mixture turned completely solid, was filtered and washed with cold water, and then recrystalized from benzene to provide trans-2-chloro-3-hydroxy-1-propenyl-mercuric chloride in 88% of theoretical yield. The vinylmercuric chloride is shown in the first shown reaction wherein R and R' are hydrogen.

Thereafter the carbonylation reaction was conducted in the following manner. Anhydrous lithium chloride (20 mmol), anhydrous cupric chloride (20 mmol) and palladium chloride (0.1 mmol) and 100 ml. of ether were added to a well dried 250 ml round bottom flask containing a septum inlet and carbon monoxide inlet tube. The flask was cooled to −78° C. and 10 mmol of trans-2-chloro-3-hydroxy-1-propenyl mercuric chloride was added. The flask was flushed thoroughly with carbon monoxide and the well-stirred reaction mixture was then allowed to slowly warm to room temperature over a four hour period. It was thereafter stirred overnight while maintaining a slight positive pressure of carbon monoxide. Ether and activated carbon were added to the reaction mixture which was filtered, washed with saturated ammonium chloride and dried over anhydrous sodium sulfate.

Filtration and evaporation of the solvent gave an isolated yield of β-chlorobutenolide of 96% of theoretical. Melting point analysis of the β-chlorobutenolide showed a melting point within the range of 52.5° to 53° C.

Thereafter the β-chlorobutenolide was treated with a dimethyl cuprate reagent. Two equivalents of methyl lithium were added to one equivalent of cuprous iodide-tributyl phosphine complex at 0° C. and the reaction mixture was cooled to −78° C. The β-chlorobutenolide was added and stirred over a 10 minute period after which the reaction mixture was quenched with ammonium chloride solution. The resulting compound had the β-chloro moiety removed and a methyl group substituted to provide β-methyl-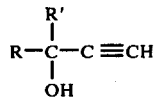,β-butenolide.

When in the above example mercuric bromide or iodide are substituted for the chloride substantially similar results, in that the corresponding bromo or iodo substituted compounds are prepared, are achieved. In like manner substantially identical results are achieved when other solvents such as methyl alcohol, and other noble metal catalysts are utilized.

When in the above example the carbonylation reaction was promoted by use of 10 mmol. of palladium chloride and no cupric chloride was employed as a reoxidant, substantially similar results were obtained.

What is claimed is:

1. A method of preparing B-halobutenolide, and gamma substituted derivatives thereof, said method comprising, reacting a compound of the formula:

$$R-\underset{\underset{OH}{|}}{\overset{\overset{R'}{|}}{C}}-C\equiv CH$$

wherein R and R' are organic moieties selected to represent the gamma substituents of the particular butenolide being prepared with a mercuric halide to provide a vinylmercuric halide, and carbonylating said vinylmercuric halide, in the presence of a carbonylating agent selected from the group consisting of noble metals and noble metal salts to provide B-halobutenolide or a gamma substituted derivative thereof.

2. The method of claim 1 wherein R and R' are selected from the group consisting of alkyl, aryl, substituted alkyl, substituted aryls, aralkyls, and substituted aralkyls.

3. The method of claim 1 wherein said mercuric halide is mercuric chloride.

4. The method of claim 3 wherein said mercuric halide is reacted with said compound of the formula:

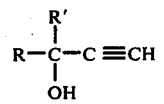

in an aqueous solvent.

5. The method of claim 4 wherein said aqueous solvent includes dissolved sodium chloride.

6. The method of claim 5 wherein said carbonylating occurs in the presence of a noble metal catalyst.

7. The method of claim 6 wherein said carbonylating occurs in the presence of a polar organic solvent which is inert to the reaction ingredients.

8. The reaction of claim 7 wherein said vinylmercuric chloride is cooled to temperatures below 0° C., and carbonylation occurs by flushing said vinylmercuric chloride with carbon monoxide.

9. A method of preparing B-halobutenolides, said method comprising,
reacting propargyl alcohol with a mercuric halide to provide a vinylmercuric halide, and
carbonylating said vinylmercuric halide, in the presence of a carbonylating agent selected from the group consisting of a noble metal and noble metal salts, to provide a B-halobutenolide.

10. A method of preparing B-chlorobutenolide, said method comprising,
reacting propargyl alcohol with mercuric chloride to provide vinylmercuric chloride, and
carbonylating said vinylmercuric chloride, in the presence of a carbonylating agent selected from the group consisting of noble metals and noble metal salts, to provide B-chlorobutenolide.

11. A method of preparing B-halobutenolides from trans-2halo-3-hydroxy-1-propenyl-mercuric halide, or substituted derivatives thereof, said method comprising, carbonylating said trans-2-halo-3-hydroxy-1-propenyl-mercuric halide, or a substituted derivative thereof, in the presence of carbonylating agent selected from the group consisting of noble metals and noble metal salts, to provide B-halobutenolides.

* * * * *